United States Patent [19]

Smith et al.

[11] Patent Number: 5,452,720
[45] Date of Patent: Sep. 26, 1995

[54] METHOD FOR TREATING BRAIN TUMORS

[75] Inventors: Donald O. Smith, Lexington; Alan P. Sliski, Lincoln; Kenneth J. Harte, Carlisle; Peter J. Biggs, Winchester; John F. Beatty, Watertown, all of Mass.

[73] Assignee: Photoelectron Corporation, Waltham, Mass.

[21] Appl. No.: 104,338

[22] Filed: Aug. 9, 1993

Related U.S. Application Data

[63] Continuation-in-part of Ser. No. 955,494, Oct. 2, 1992, Pat. No. 5,369,679, which is a continuation-in-part of Ser. No. 577,883, Sep. 5, 1990, Pat. No. 5,153,900.

[51] Int. Cl.$^6$ .............................. A61B 6/12; A61N 5/10; A61M 36/00; H01J 35/32
[52] U.S. Cl. .................. 128/653.1; 606/130; 378/65; 378/207; 600/1; 600/3
[58] Field of Search ................. 128/653.1, 659; 606/130; 600/1, 3, 7; 378/65, 207

[56] References Cited

U.S. PATENT DOCUMENTS

| | | | |
|---|---|---|---|
| Re. 34,421 | 10/1993 | Parker et al. | 378/65 |
| 1,981,583 | 11/1934 | Craig. | |
| 2,748,294 | 5/1956 | Reinger. | |
| 3,714,486 | 1/1973 | McCrary. | |
| 3,752,990 | 8/1973 | Fischer. | |
| 3,794,840 | 2/1974 | Scott | 378/65 |
| 3,920,999 | 11/1975 | Drexler et al.. | |
| 4,104,531 | 8/1978 | Weiss. | |
| 4,104,532 | 8/1978 | Weiss. | |
| 4,109,154 | 8/1978 | Taumann. | |
| 4,117,334 | 9/1978 | Strauts. | |
| 4,157,475 | 6/1979 | Stock et al.. | |
| 4,205,251 | 5/1980 | Zwep. | |
| 4,344,181 | 8/1982 | Baecklund. | |
| 4,517,472 | 5/1985 | Ruitberg et al.. | |
| 4,563,769 | 1/1986 | Madsen. | |
| 4,608,977 | 9/1986 | Brown. | |
| 4,638,798 | 1/1987 | Shelden et al. | 606/130 |
| 4,646,338 | 2/1987 | Skillicorn. | |
| 4,694,480 | 9/1987 | Skillicorn. | |
| 4,789,997 | 12/1988 | Madsen et al.. | |
| 4,856,036 | 8/1989 | Malcolm et al.. | |
| 4,869,247 | 9/1989 | Howard, III et al. | 606/130 |
| 4,924,485 | 5/1990 | Hoeberling. | |
| 5,065,417 | 11/1991 | Behringer et al. | 378/54 |
| 5,090,043 | 2/1992 | Parker et al.. | |
| 5,095,217 | 3/1992 | Attix | 250/491.1 |
| 5,116,344 | 5/1992 | Sundquist. | |
| 5,116,345 | 5/1992 | Jewell et al.. | |
| 5,153,900 | 10/1992 | Nomikos et al. | 378/65 |
| 5,154,723 | 10/1992 | Kobuta et al. | 606/130 |
| 5,165,093 | 11/1992 | Miller et al.. | |
| 5,189,687 | 2/1993 | Bova et al. | 378/65 |
| 5,250,019 | 10/1993 | McGinley | 600/1 |
| 5,261,406 | 11/1993 | MacKay et al. | 128/653.1 |
| 5,300,080 | 4/1994 | Clayman et al. | 606/130 |
| 5,339,812 | 8/1994 | Hardy et al. | 600/7 |
| 5,354,314 | 10/1994 | Hardy et al. | 606/130 |
| 5,373,844 | 12/1994 | Smith et al. | 128/653.1 |

*Primary Examiner*—Krista M. Pfaffle Zele
*Attorney, Agent, or Firm*—Lappin & Kusmer

[57] ABSTRACT

A method of treating brain tumors in a patient, comprising the steps of: identifying and locating a brain tumor in vivo by affixing a stereotactic frame to the head of the patient, performing a computer tomographic (CT) scan of the skull of the patient to determine the location, size, and shape of the tumor with respect to the stereotactic frame, performing a biopsy by inserting an extraction tool along a path measured with respect to the frame to the tumor location, extracting a tissue from the location, removing the needle and the extracted tissue and analyzing the tissue; implanting at least a portion of an adjustable x-ray radiation source in the patient proximate the tumor, the adjustable radiation source including an electron beam source outside the head of the patient, and directing an electron beam produced by the source outside the head of the patient along the path to the location; and controlling the source to generate an x-ray radiation pattern characterized by a spatial and temporal distribution, to selectively irradiate the tumor.

7 Claims, 12 Drawing Sheets

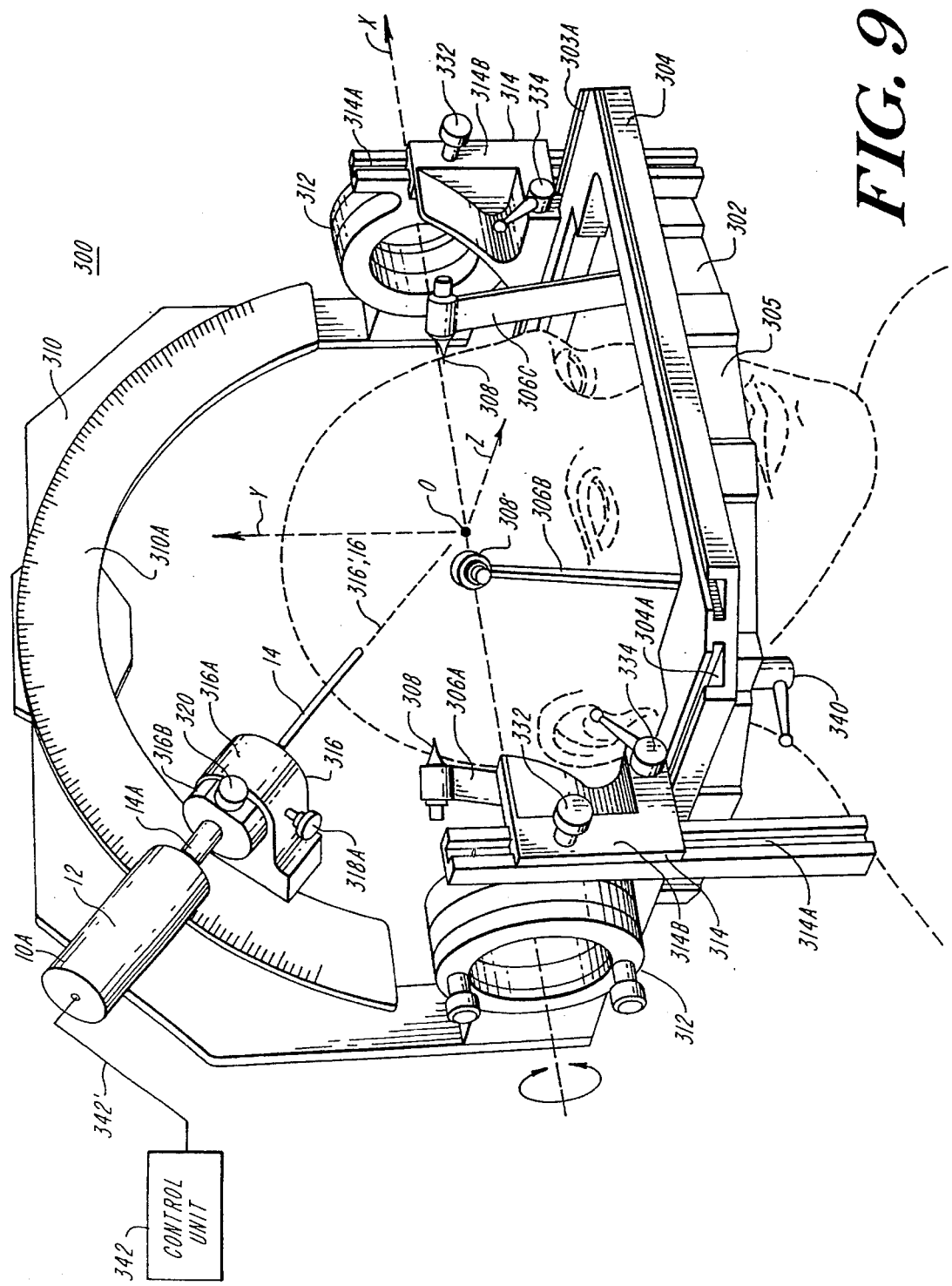

METHOD FOR TREATING BRAIN TUMORS

REFERENCE TO RELATED APPLICATION

This application is a continuation-in-part of U.S. patent application Ser. No. 955,494, now U.S. Pat. No. 5,369,679, entitled LOW POWER X-RAY SOURCE WITH IMPLANTABLE PROBE FOR TREATMENT OF BRAIN TUMORS, filed Oct. 2, 1992, assigned to the assignee of the present application, which is a continuation-in-part of U.S. patent application Ser. No. 577,883, now U.S. Pat. No. 5,153,900, entitled "Miniaturized Low Power X-Ray Source," filed Sep. 5, 1990, assigned to the assignee of the present application.

BACKGROUND OF DISCLOSURE

The present invention relates to methods of treating brain tumors, particularly using a low power, programmable x-ray source for use in delivering low-levels of substantially constant or intermittent x-rays to a specified region.

Conventional medical x-ray sources are large, fixed position machines. Generally, the head of the x-ray tube is placed in one room and the control console in an adjoining area, with a protective wall, equipped with a viewing window, separating the two. The x-ray tube typically is approximately 20 to 35 centimeters (cm) long, and approximately 15 cm in diameter. A high voltage power supply is housed within a container located in a corner of the room containing the x-ray tube. Patients are brought to the machine for diagnostic, therapeutic, or palliative treatment.

Diagnostic x-ray machines are typically operated at voltages below 150 kilovolts (kV), and at currents from approximately 25 to 1200 milliamps (mA). By contrast, the currents in therapeutic units typically do not exceed 20 mA at voltages which may range above 150 kV. When an x-ray machine is operated at nominal voltages of 10 to 140 kV, the emitted x-rays provide limited penetration of tissue, and are thus useful in treating skin lesions. At higher voltages (approximately 250 kV), deep x-ray penetration is achieved, which is useful in the treatment of major body tumors. Super voltage machines, operable in the 4 to 8 megavolt (MV) region, are used to ablate or destroy all types of tumors, except superficial skin lesions.

A conventional x-ray tube includes an anode, grid, and cathode assembly. The cathode assembly generates an electron beam which is directed to a target, by an electric field established by the anode and grid. The target in turn emits x-ray radiation in response to the incident electron beam. The radiation absorbed by a patient generally is that which is transmitted from the target in the x-ray tube through a window in the tube, taking into account transmission losses. This window typically is a thin section of beryllium, or other suitable material. In a typical x-ray machine, the cathode assembly consists of a thoriated tungsten coil approximately 2 mm in diameter and 1 to 2 cm in length which, when resistively heated with a current of 4 amps (A) or higher, thermionically emits electrons. This coil is surrounded by a metal focusing cup which concentrates the beam of electrons to a small spot on an opposing anode which also functions as the target. In models having a grid, it is the grid which both controls the path of the electron beam and focuses the beam.

The transmission of an electron beam from cathode to anode is influenced by electron space charge forces which tend to become significant in conventional x-ray machines at currents exceeding 1 A. In such conventional machines, the beam is focused on the anode to a spot diameter ranging anywhere from 0.3 to 2.5 millimeters (mm). In many applications, most of the energy from the electron beam is converted into heat at the anode. To accommodate such heating, high power medical x-ray sources often utilize liquid cooling and a rapidly rotating anode, thereby establishing an increased effective target area, permitting a small focal spot while minimizing the effects of localized heating. To achieve good thermal conductivity and effective heat dissipation, the anode typically is fabricated from copper. In addition, the area of the anode onto which an electron beam is incident requires a material of high atomic number for efficient x-ray generation. To meet the requirements of thermal conductivity, effective heat dissipation, and efficient x-ray generation, a tungsten alloy typically is embedded in the copper.

In use, the total exposure from an x-ray source is directly proportional to the time integral of the electron beam. During relatively long exposures (e.g. lasting 1 to 3 seconds), the anode temperature may rise sufficiently to cause it to glow brightly, accompanied by localized surface melting and pitting which degrades the radiation output. However, thermal vaporization of the tube's coiled cathode filament is most frequently responsible for conventional tube failure.

While the efficiency of x-ray generation is independent of the electron beam current, it is highly dependent on the acceleration voltage. Below 60 kV, only a few tenths of one percent of the kinetic energy from an electron is converted to x-rays, whereas at 20 MV that conversion factor rises to 70 percent. An emitted x-ray spectrum is composed in part of discrete energies characteristic of transitions between bound electron energy levels of the target element. The spectrum also includes an x-ray energy continuum, known as bremsstrahlung, which is caused by acceleration of the beam electrons as they pass near target nuclei. The maximum energy of an x-ray cannot exceed the peak energy of an electron in the beam. Further, the peak of the bremsstrahlung emission curve occurs at approximately one-third the electron energy.

Increasing the electron current results in a directly proportional increase in x-ray emission at all energies. However, a change in beam voltage results in a total x-ray output variation approximately equal to the square of the voltage, with a corresponding shift in peak x-ray photon energy. The efficiency of bremsstrahlung radiation production increases with the atomic number of the target element. The peak output in the bremsstrahlung curve and the characteristic spectral lines shift to higher energies as the atomic number of the target increases. Although tungsten ($Z=74$) is the most common target material used in modern tubes, gold ($Z=79$) and molybdenum ($Z=42$) are used in some specialty tubes.

X-rays interact in several ways with matter. For biological samples, the following two types of interactions are most important: Compton scattering of moderate-energy x-rays with outer shell electrons; and, photoionizing interactions of inner shell electrons. In these processes, the probability of atom ionization decreases with increasing photon energy in both soft tissue and bone. For the photoelectric effect, this relationship follows an inverse third-power law.

One disadvantage of present x-ray devices used for therapy is the high voltage required when directed to soft tissue within or beneath bone. One example is in directing x-rays to areas of the human brain, which is surrounded by bone. High energy x-rays are required to penetrate the bone, but often damage the skin and brain tissue. Another example in radiation therapy is in directing the x-rays to soft tissue located within the body cavity, couched among other soft tissue, or within an internal calciferous structure. Present high-voltage machines are limited in their ability to selectively provide desired x-ray radiation to such areas.

Another disadvantage of the high voltage output of present x-ray sources is the damage caused to skin external to the affected organ or tissue. Therefore, high voltage devices of present systems often cause significant damage not only to the target region or tissue, but also to all surrounding tissue and surface skin, particularly when used for human tumor therapy. However, since present devices apply x-ray radiation to target regions internal to a patient from a source external to the target region, such incidental tissue damage is practically unavoidable.

Specifically as to brain tissue, which lacks any substantial regenerative ability, the treatment of brain tumors requires precise techniques to bring about specific tissue destruction. The use of conventional x-ray devices in brain tumor therapy often lacks the precision needed in volumetric irradiation, resulting in the damage of non-cancerous tissue of the brain and associated glandular structures.

An alternative form of tumor therapy, called brachytherapy, involves implanting encapsulated radioisotopes in or near the tumor to be treated. While such use of radioisotopes may be effective in treating certain types of tumors, introduction of the isotopes requires invasive procedures which have potential side-effects, such as the possibility of infection. Moreover, brain swelling may occur in some applications because the emission from the isotope cannot be controlled. Further, there is no ability to provide selective control of time dosage or radiation intensity. Handling and disposal of such radioisotopes involves hazards to both the individual handler and the environment.

Invasive techniques of the brain require precise control of irradiation through the choice and concentration of isotopes used. Intracranial penetration poses a significant risk as is well known in the art.

In view of the above requirements and limitations to the use of x-rays from present machines in therapeutic, diagnostic, palliative, or evaluative environments, there remains a need for a relatively small, easily manipulated, low-energy, x-ray device. Such a device operating at low energy and power will be suitable for many of the applications described herein.

Accordingly, it is an object of the present invention to provide an improved method for treating brain tumors.

It is another object of the present invention to provide a treatment method for brain tumors using an implantable, low-power x-ray device.

SUMMARY OF THE INVENTION

Briefly, the invention is a treatment planning and operation room procedure for a Photonic Radiosurgery Source (PRS), used to deliver single fraction doses of x-rays to small metastatic brain lesions. The procedure begins with a CT scan of the patient, with a stereotactic head frame attached, to determine tumor location, size, and shape, as well as suitable point of entry for a stereotactic biopsy. A biopsy is performed using the coordinates derived from the stereotactic frame. Preferably, while the biopsy is being performed, a series of checks are performed on the PRS to ensure that the output is optimized and in calibration. Following a short warm-up period, beam alignment and output of the PRS are checked for symmetry by a photodiode array, and for absolute calibration via ion chamber. A transfer calibration factor to convert the exposure measured in air to dose in water at 1 cm from the source is applied. Subsequent to a positive pathology report, the PRS, is coupled to the stereotactic frame and inserted into the patient, through the path of the biopsy needle. Scintillation detectors are located on either side of the head in the stereotactic frame to monitor the output of the device during the treatment. Signals from these detectors are recorded and displayed on a PC video monitor. After the treatment, similar checks of the output are made. The invention is particularly well suited for use with an easily manipulated PRS having a low-level, electron beam (e-beam) activated x-ray source of preselected, or adjustable, duration, effective energy and intensity, for example as-disclosed in U.S. Pat. No. 5,153,900, and U.S. patent application Ser. No. 955,494. The PRS (or "probe") may be fully or partially implanted into, or surface-mounted onto a desired area of a patient to irradiate a region with x-rays. As noted above the PRS "preferably assembled in combination with a reference frame, for example, a stereotactic frame, and an associated coupler for use in the treatment of brain tumors.

With the method of the invention, the apparatus operates at a relatively low voltage, for example, in the range of approximately 10 kV to 90 kV, with small electron currents, for example, in the range of from approximately 1 nA to 100 mA. To achieve a desired radiation pattern over a desired region, while minimally irradiating other regions, x-rays may be emitted from a nominal, or effective "point" source located within or adjacent to the desired region-to-be-irradiated. In some applications, a low dose rate of x-rays irradiates any part of the desired region, either continually or periodically, over extended periods of time. For use with a reference frame for treatment of brain tumors, a high dose rate for single dose irradiation is generally preferred.

The PRS apparatus preferably includes a controllable, or programmable, power supply located outside the desired region-to-be-irradiated to enable variations in voltage, current, and timing of an electron beam. The electron beam is controlled to pass along a desired beam axis and to be incident on a target which is preferably located in the patient's body. The axis may be straight, or curved. The composition and/or geometry of the target, or x-ray emitting, material is selected to provide a customized pattern of x-rays. Shielding at the emission site, or around the target, further enables control of the energy and spatial profile of the x-ray emission to match the preselected distribution of radiation throughout the desired region. The use of a small target, relative to the cross-sectional area of the x-ray producing electron beam, can provide a stable and reproducible source of x-rays.

Thus, the present invention provides a method of treating malignant cells, such as found in tumors, in vivo, utilizing the apparatus described above. Generally, the method involves identifying and locating malignant cells with a device generally available in the art, such as by computed tomography (CT) scanning or magnetic resonance imaging (MRI). A needle-type biopsy of the tumor may be performed to confirm the diagnosis. Then the region of treatment is selected and the radiation dosage determined. Such radiation treatment planning involves defining the size and shape of the tumor determining precisely its location in the body, identifying radiation-sensitive critical biological structures surrounding the tumor, deciding on the proper radiation dose distribution in the tumor and surrounding tissue and the entry path in to the tumor of the implanted performed manually using CT or MRI data. However, for more complex geometries, close-by critical structures, or higher precision procedures, computer-based "3-D" imagery is performed. In that case, tumors and critical structures are, for example, manually or semiautomatically segmented on a series of digitized CT scans, and a 3-D composite is rendered, which allows viewing the tumor from any direction. Various software systems have been developed for radiosurgical procedures, such as for the linac and gamma knife, and some are commercially available. For example, Radionics Software Applications of Brookline, Mass. offers for sale software which images a CRW and BRW stereotactic frame affixed to a graphically transparent skull. Isodose profiles are overlaid on the tumor and other brain tissue. Similar software may be used with the invention disclosed in U.S. patent application Ser. No. 955,494, which effects imaging with respect to a stereotactic frame, for use with the x-ray-radiating electron beam target imbedded in the tumor. Isodose contours around the target are superimposed on the tumor and adjacent tissue. The absolute radiation dosage delivered along each contour is determined by experimental dosimetry performed to calibrate the probe. In these tests, the dose is measured at multiple locations around the target immersed in water or a biological tissue-simulating phantom. Such plastic, "solid water," phantoms are commercially available (RMI, Middleton, Wis.) and simulate various body tissues, e.g., soft tissue of the brain. Either thermoluminescent detectors (TLD) or calibrated x-ray sensitive film (e.g., gafchromic film from Far West Technologies, Goleta, Calif.) can be positioned in the solid water to measure the dose directly. Using the imaging and dosimetry results from the radiation treatment planning, a low-power electron beam source and a selectively shaped x-ray radiation pattern generating target and shield assembly are positioned within or proximal to a region containing the cells to-be-irradiated, generally tumor cells, for example, in conjunction with a stereotactic frame assembly, such as disclosed in U.S. patent application Ser. No. 955,494. Other positioning assemblies, or methods, may be used.

Pursuant to the present invention, the target and shield assembly geometry and materials are shaped and selected in accordance with the characteristics of the desired region-to-be-irradiated. A programmable power supply is provided, which may be used to vary the voltage, current, and duration of the electron beam source to establish, in accordance with dosimetry information, a desired electron beam which is directed to the desired region-to-be-irradiated. Finally, x-rays emitted from the target and shield assembly are transmitted to the desired region-to-be-irradiated for selective destruction of the cells in that region.

In particular, the treatment of a tumor can be carried out utilizing an apparatus of the present invention comprising the combination of a low-power x-ray source for generation of a controllable irradiation pattern, with a device for accurately positioning the x-ray source in the body. The x-ray source can thus be precisely located near or in the tumor.

BRIEF DESCRIPTION OF DRAWINGS

The foregoing and other objects of this invention, the various features thereof, as well as the invention itself, may be more fully understood from the following description, when read together with the accompanying drawings in which:

FIG. 8A is a cross-section view of the assembly of FIG. 8, taken along lines 8a;

FIG. 9 is a perspective view of a brain tumor x-ray treatment system incorporating a stereotactic frame for positioning the x-ray source;

Like numbered elements in each FIGURE represent the same or similar elements.

DESCRIPTION OF THE PREFERRED EMBODIMENTS

The present invention is a method for treating brain tumors, particularly adapted for use with a relatively small, electron-beam activated, low power x-ray apparatus. The method is advantageously used where the x-ray apparatus is coupled to a stereotactic frame affixed to a patient's head. The method may be used for therapeutic or palliative radiation treatment of tumors, or for other purposes.

Generally, the preferred apparatus for use with the present invention includes an electron-beam (e beam) activated x-ray source which operates at relatively low voltages, i.e. in the range of approximately 10 kV to 90 kV, and relatively small electron beam currents, i.e. in the range of approximately 1 nA to 100 mA. At those operating voltages and currents, the x-ray output is relatively low, and the apparatus may be made quite small and be adapted for implantation in medical therapeutic applications. In view of the low level x-ray output, adequate tissue penetration and cumulative dosage may be attained by locating the x-ray source adjacent to or within the region to be irradiated. Thus, the x-rays are emitted from a well-defined, small source located within or adjacent to the region to be irradiated. In the preferred embodiment, a low dose rate of x-rays may be applied to any part of a tumor, either continually or periodically, over extended periods of time, e.g., up to one month. In use with a stereotactic frame for the treatment of brain tumors, a high dose rate may be applied to a tumor for shorter periods of time (i.e., on the order of 5 minutes to 3 hours).

The present invention provides interstitial radiotherapy similar to that achieved with implanted capsules, needles, tubes, and threads containing natural or artificial radioactive isotopes, known as brachytherapy. However, a programmable power supply may be included in the x-ray source of the present apparatus to vary energy, intensity, and duration of the radiation. This differs from brachytherapy in that the intensity and penetration depth of the x-rays may be changed without surgically or invasively replacing the isotopes. Furthermore, the present invention is not limited by the half-life of a particular isotope, and does not pose a radiation hazard when turned off.

Figure 1:
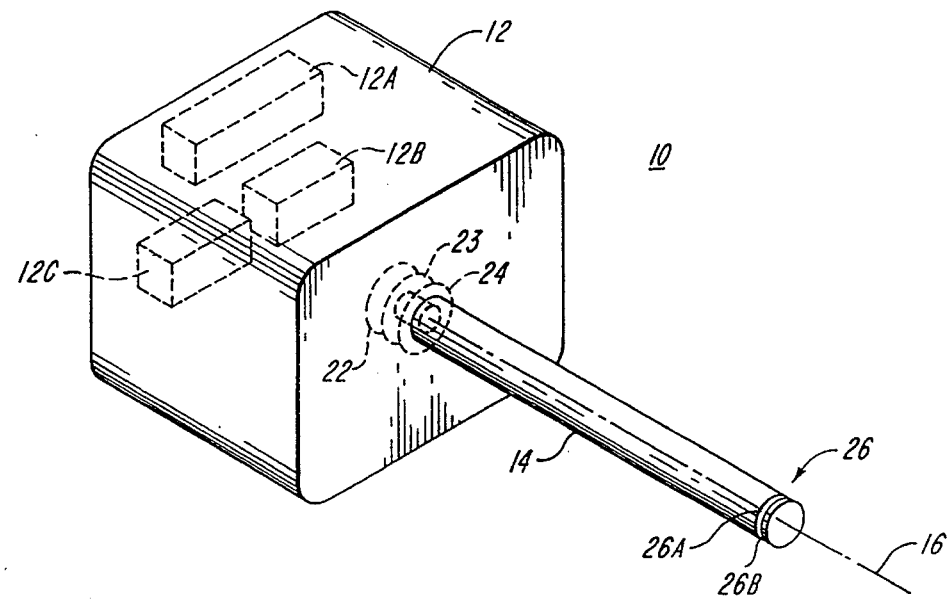
FIG. 1 is a perspective view of a low power x-ray source embodying the present invention.

FIG. 1 shows an x-ray apparatus 10 for use with the present invention. Apparatus 10 includes a housing 12 and an elongated cylindrical probe 14 extending from housing 12 along a reference axis 16. The housing 12 encloses a high voltage power supply 12A (illustrated in electrical schematic form in FIGS. 6 and 7). The probe 14 is a hollow tube having an electron beam generator (cathode) 22 adjacent to the high voltage power supply 12A. Cathode 22 is located in close proximity to an annular focusing electrode 23 typically at the same potential as the cathode 22. An annular anode 24 is positioned approximately 0.5 cm or more from the annular focusing electrode 23. A hollow, tubular probe 14 extends along the same axis as the cathode, grid, and the hole in the anode. Probe 14 is integral with the housing 12 and extends toward a target assembly 26. In various embodiments, parts of the probe 14 may be selectively shielded to control the spatial distribution of x-rays. In addition, the probe 14 may be magnetically shielded to prevent external magnetic fields from deflecting the beam away from the target.

The electron beam generator 22 may include a thermionic emitter (driven by a floating low voltage power supply) or a photocathode (irradiated by an LED or laser source). The high voltage power supply establishes an acceleration potential difference between the cathode of generator 22 and the grounded anode 24 so that an electron beam is established along the reference axis 16, through the center hole of the anode and to the target assembly 26, with the region between anode 24 and the target assembly 26 being substantially field free. The beam generation and acceleration components are adapted to establish a thin (e.g. 1 mm or less in diameter) electron beam within the probe 14 along a nominally straight axis 16.

In a preferred embodiment, the probe 14 is a hollow, evacuated beryllium (Be), Mo-Re or mu metal cylinder 15 cm long, with an interior diameter of 2 mm, and an exterior diameter of 3 mm. The target assembly 26 includes an emission element consisting of a small beryllium (Be) window element 26a coated on the side exposed to the incident electron beam with a thin film or layer 26b of a high-Z element, such as tungsten (W) or gold (Au). By way of example, with electrons accelerated to 30 keV-, a 2.2 micron thick tungsten film absorbs substantially all the incident electrons, while transmitting approximately 95% of any 30 keV-, 88% of any 20 keV-, and 83% of any 10 keV- x-rays generated in that layer. In a preferred form of the x-ray source, the beryllium window element 26a is 0.5 mm thick with the result that 95% of these x-rays generated in directions normal and toward the substrate, and having passed through the tungsten target, are then transmitted through the beryllium substrate and outward at the distal end of probe 14. While the window element 26a shown in FIG. 3b is in the form of a disc, other shaped elements may be used, such as those having hemispherical or conical outer surfaces.

For use with some forms of the invention, the window element 26a assembly may include a multiple layer film 26b, where the differing layers may have different emission characteristics. By way of example, the first layer may have an emission (vs. energy) peak at a relatively low energy, and the second (underlying) layer may have an emission (vs. energy) peak at a relatively high energy. With this form, a low energy electron beam may be used to generate x-rays in the first layer (to achieve a first radiation characteristic) and high energy electrons may be used to penetrate through to the underlying layer (to achieve a second radiation characteristic). As an example, a 0.5 mm wide electron beam is emitted at the cathode and accelerated to 30 keV- through the anode, with 0.1 eV transverse electron energies, and arrives at the target 26 sixteen centimeters downstream from the anode, with a beam diameter of less than 1 mm at the target. X-rays are generated in the target material in accordance with preselected beam voltage, current, and target composition. The x-rays thus generated pass through the beryllium window element 26a in the probe with minimized loss in energy. The window element 26a may be made of carbon, beryllium (Be), or other suitable material which permits x-rays to pass with a minimum loss of energy. An optimal material for window element 26a is diamond, since that material is an excellent heat conductor. In some embodiments, a discrete x-ray transmissive window separate from the target assembly 26 may be used. Using these parameters, the resultant x-rays have sufficient energy to penetrate into soft tissues to a depth of a centimeter or more, the exact depth dependent upon the x-ray energy distribution.

The apparatus of FIG. 1 is particularly adapted for full implantation into a patient, where the housing 12 has a biocompatible outer surface and encloses both a high voltage power supply circuit 12A for establishing a drive voltage for the beam generator 22, and an associated battery 12B for driving that circuit 12A. In this case, an associated controller 12C establishes control of the output voltage of the high power supply circuit 12A, in the manner described below.

The apparatus of FIG. 1 may also be used in a manner where only the probe 14 is inserted into a patient while the housing remains outside the patient, i.e., a transcutaneous form. In the latter form, the various elements shown within housing 12 may alternatively be remotely located.

Figure 2:
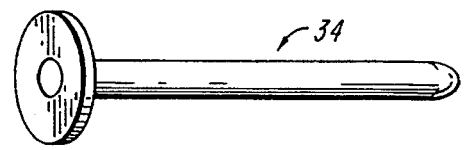
FIG. 2 is a schematic representation of a sheath adapted for use with the apparatus of FIG. 1.

In the transcutaneous form, the apparatus 10 may be used with an elongated closed end (or cup-shaped) sheath 34, as shown in FIG. 2, having a biocompatible outer surface, for example, fabricated of medical grade aliphatic polyurethane, as manufactured under the trademark Tecoflex® by Thermedics, Inc., Woburn, Mass. With this configuration, the probe 14 is first inserted into the sheath 34. The sheath 34 and probe 14 are then inserted into the patient through the skin. Alternatively, a port may be inserted through the skin and attached to it, as for example a Dermaport® port manufactured by Thermedics Inc., Woburn, Mass. The probe 14 is then inserted into the port.

The lining of the sheath or port can be configured as an x-ray shield by introducing barium sulfate or bismuth trioxide, or other x-ray shielding materials, into the sheath. If necessary, the probe 14 and housing 12 can be secured to the patient's body to prevent any relative motion during the extended time of treatment. An exemplary sheath 34 is shown in FIG. 2.

In one embodiment of the apparatus, the main body of the probe 14 can be made of a magnetically shielding material such as a mu-metal. Alternatively, the probe 14 can be made of a non-magnetic metal, preferably having relatively high values for Young's modulus and elastic limit. Examples of such material include molybdenum, rhenium or alloys of these materials. The inner or outer surface of probe 14 can then be coated with a high permeability magnetic alloy such as permalloy (approximately 80% nickel and 20% iron), to provide magnetic shielding. The x-ray apparatus 10 can then be used in environments in which there are dc and ac magnetic fields due to electrical power, the field of the earth, or other magnetized bodies nominally capable of deflecting the electron beam from the probe axis.

In implantable configurations, the power supply 12A and target assembly 26 are preferably enclosed in a metal capsule to prevent current flow from the x-ray source to the patient. The closed housing 12 and probe 14 are, thus, encapsulated in a continuous outer shell of appropriate shielding material such as those mentioned previously.

The high voltage power supply 12A in each of the illustrated embodiments preferably satisfies three criteria: 1) small in size; 2) high efficiency to enable the use of battery power; and 3) independently variable x-ray tube voltage and current to enable the unit to be programmed for specific applications. A high-frequency, switch-mode power converter is used to meet these requirements. The most appropriate topology for generating low power and high voltage is a flyback voltage converter working in conjunction with a high voltage, Cockroft-Walton-type multiplier. Low-power dissipation, switch-mode power-supply controller-integrated circuits (IC) are currently available for controlling such topologies with few ancillary components.

In order to provide active control of the x-rays, a preferred embodiment of the present invention establishes independent control of cathode voltage and current without the use of a grid electrode. In that form of the invention, an rf ohmic heating current is provided to a thermionic cathode 22, preferably using a transformer-coupled 0.6 volt, 0–300 mA filament power supply floating at the cathode potential of 40 kV.

Figure 3A:
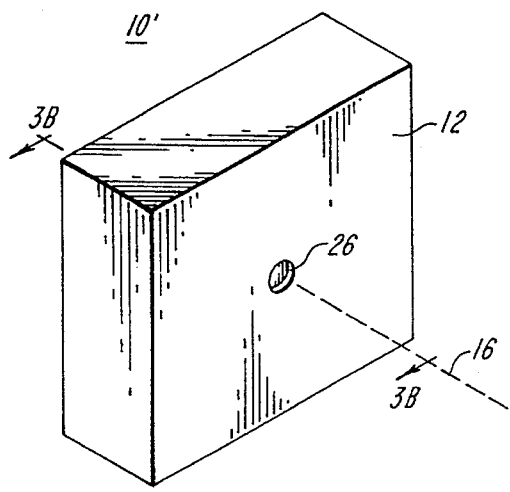
FIGS. 3A and 3B are a perspective view and sectional view, respectively, of a surface-mountable apparatus embodying the present invention.
Figure 3B:
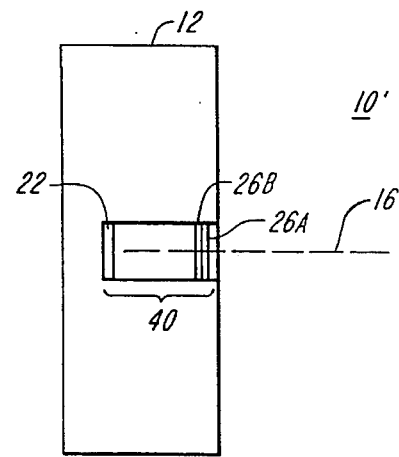

FIGS. 3A and 3B show an alternative embodiment 10' of the invention adapted for superficial usage, that is for direct placement on the skin of a patient. This form of the invention is particularly useful for x-ray treatment of skin lesions or tumors, or other dermatological applications. In FIGS. 3A and 3B, elements that correspond to elements in the embodiment of FIG. 1 are denoted with the same reference designations. Apparatus 10' generates an electron beam in a channel 40 enclosed within housing 12, where that channel 40 corresponds to probe 14. In the present embodiment, of FIGS. 3A and 3B, the target 26 (elements 26a and 26b) functions as the anode as well as an x-ray emitter. Otherwise, the apparatus 10' is similar to apparatus 10. With the configuration of FIGS. 3A and 3B, low power x-rays may be directed to a desired skin region of a patient.

In all of the above-described embodiments, the x-ray emission element of the target assembly is adapted to be adjacent to or within the region to be irradiated. The proximity of the emission element to the targeted region, e.g. the tumor, eliminates the need for the high voltages of presently used machines, to achieve satisfactory x-ray penetration through the body wall to the tumor site. The low voltage also concentrates the radiation in the targeted tumor, and limits the damage to surrounding tissue and surface skin at the point of penetration. For example, the delivery of 4000 rads, as is required after a mastectomy, with a 40 kV, 20 mA electron beam, may require approximately 1 to 3 hours of radiation. However, since the x-ray source is, in this preferred embodiment, insertable proximate to, or into, the region-to-be-irradiated risk of incidental radiation exposure to other parts of the patient's body is significantly reduced.

Further, specificity in treating tumors may be achieved by tailoring the target and shield geometry and material at the emission site. This tailoring facilitates the control of energy and the spatial profile of the x-ray emission to ensure homogenous distribution of the radiation throughout the targeted tumor.

Figure 4:
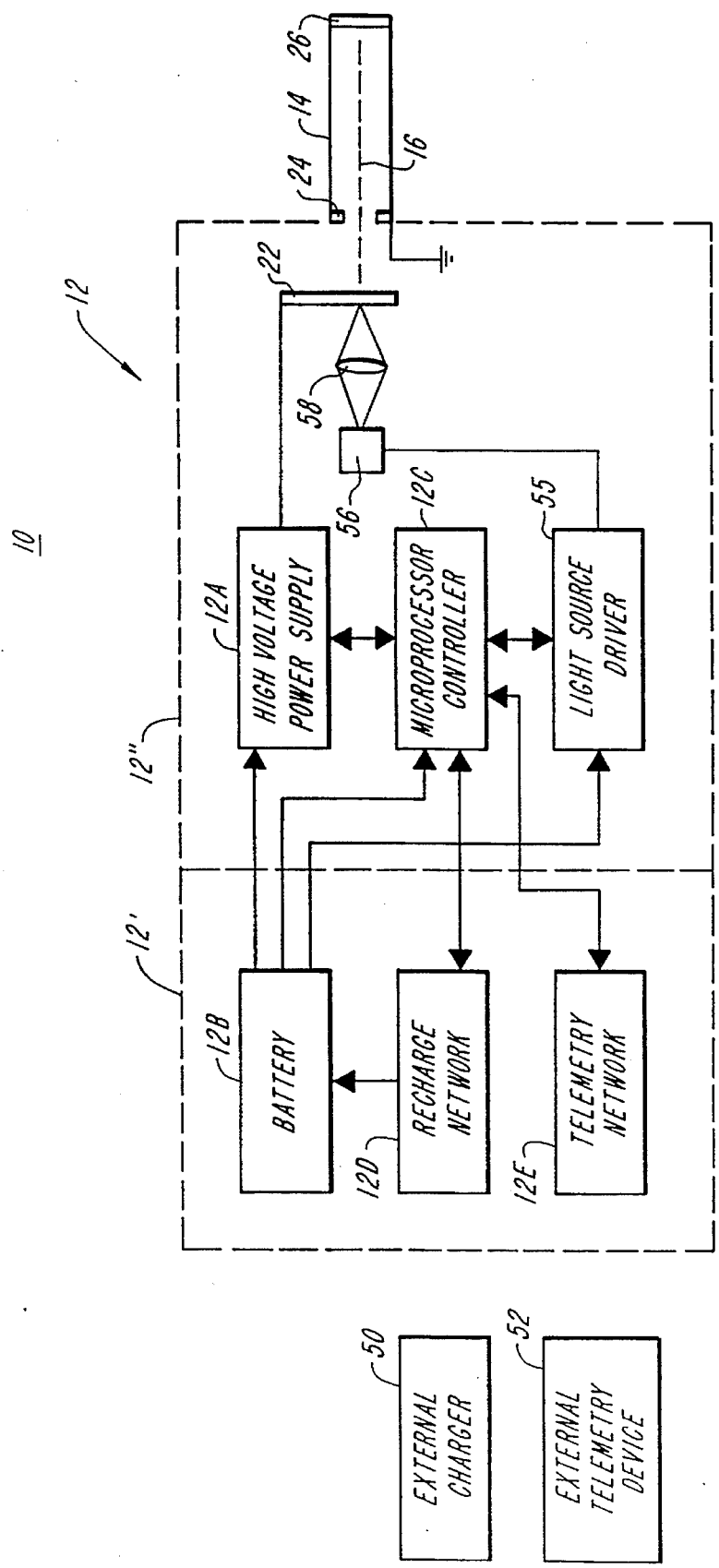
FIG. 4 is a schematic block diagram of the embodiment of FIG. 1.

FIG. 4 is a schematic representation of the x-ray source apparatus 10 shown in FIG. 1. In that configuration, the housing 12 is divided into a first portion 12' and a second portion 12". Enclosed within the first housing portion 12' is a rechargeable battery 12B, a recharge network 12D for the battery 12B, which is adapted for use with an external charger 50, and a telemetry network 12E, adapted to be responsive to an external telemetry device 52 to function in the manner described below. That portion 12' is coupled by cables to the second housing portion 12". The second housing portion 12" includes the high voltage power supply 12A, controller 12C and the probe 14, as well as the electron beam generating element 22. In the illustrated apparatus 10, the electron beam generator includes a thermionic emitter 22 driven by the power supply 12A. In operation, power supply 12A heats the thermionic emitter 22, which in turn generates electrons which are then accelerated toward the anode 24. The anode 24 attracts the electrons, but passes them through its central aperture toward the target assembly 26. The controller 12C controls the power supply 12A to dynamically adjust the cathode voltage, the electron beam current, and temporal parameters, or to provide pre-selected voltage, beam current, and temporal parameters.

In the illustrated embodiment, device 52 and network 12E cooperate to permit external control (dynamic or predetermined) control over the power supply 12A and temporal parameters. In embodiments when the housing 12" is not implanted, but where only probe 14 extends into a patient's body, the controller 12C may directly be used to control operation; in that case there is no need for network 12E.

Figure 5A:
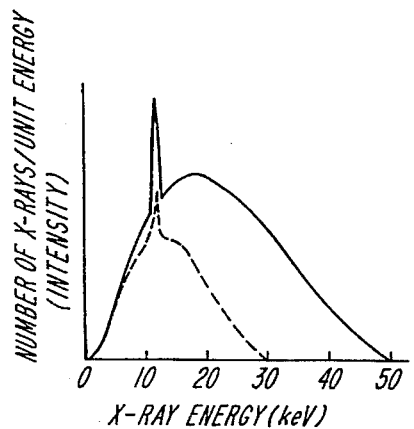
FIGS. 5A and 5B are graphical representations of the x-ray emission spectrum of tungsten- and molybdenum-targets, respectively.
Figure 5B:
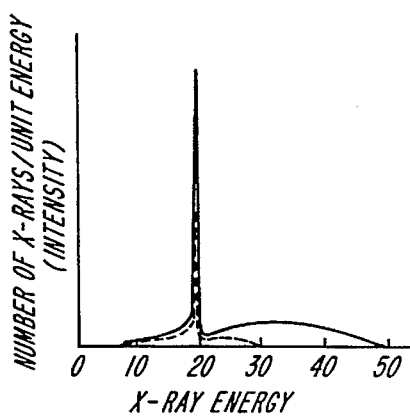

In an important aspect, the target assembly 26 may be shaped to emit x-rays in a radiation pattern having a predetermined spatial distribution, and in a predetermined spectral range. This target shaping may be achieved in part by selecting target materials of known characteristics. For example, as shown in FIGS. 5A and 5B, the emission spectrums for tungsten targets (FIG. 5A) and molybdenum targets (FIG. 5B) are distinct. FIG. 5A shows the x-ray emission spectrum from a tungsten target tube operating at 30 and 50 kV. Note that the bremsstrahlung spectrum predominates, and that x-rays are supplied in a wide energy range. FIG. 5B shows the emission spectrum from a molybdenum target tube, also operating at 30 and 50 kV. Note the near absence of bremsstrahlung x-rays. Note also that the change in tube potential from 30 to 50 kV results in a minor change in the shape of the emission spectrum from a-molybdenum target x-ray tube. By selecting the target material, depending upon the type of penetration and the targeted region to be irradiated, the x-ray emission from target assembly 26 may effectively be shaped.

Figure 6:
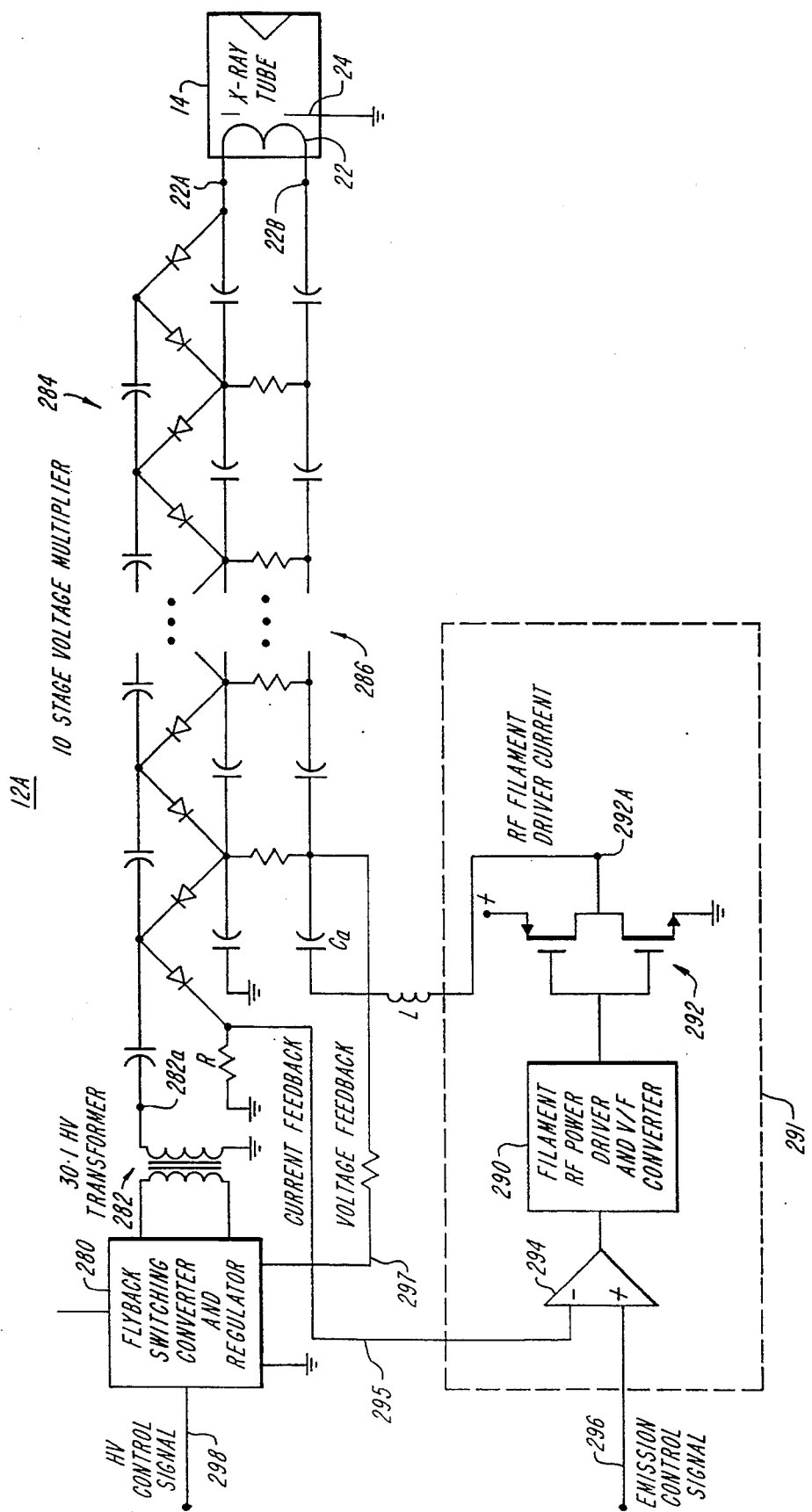
FIG. 6 is a detailed block diagram of a representative power supply of the embodiment of FIG. 1.
Figure 7:
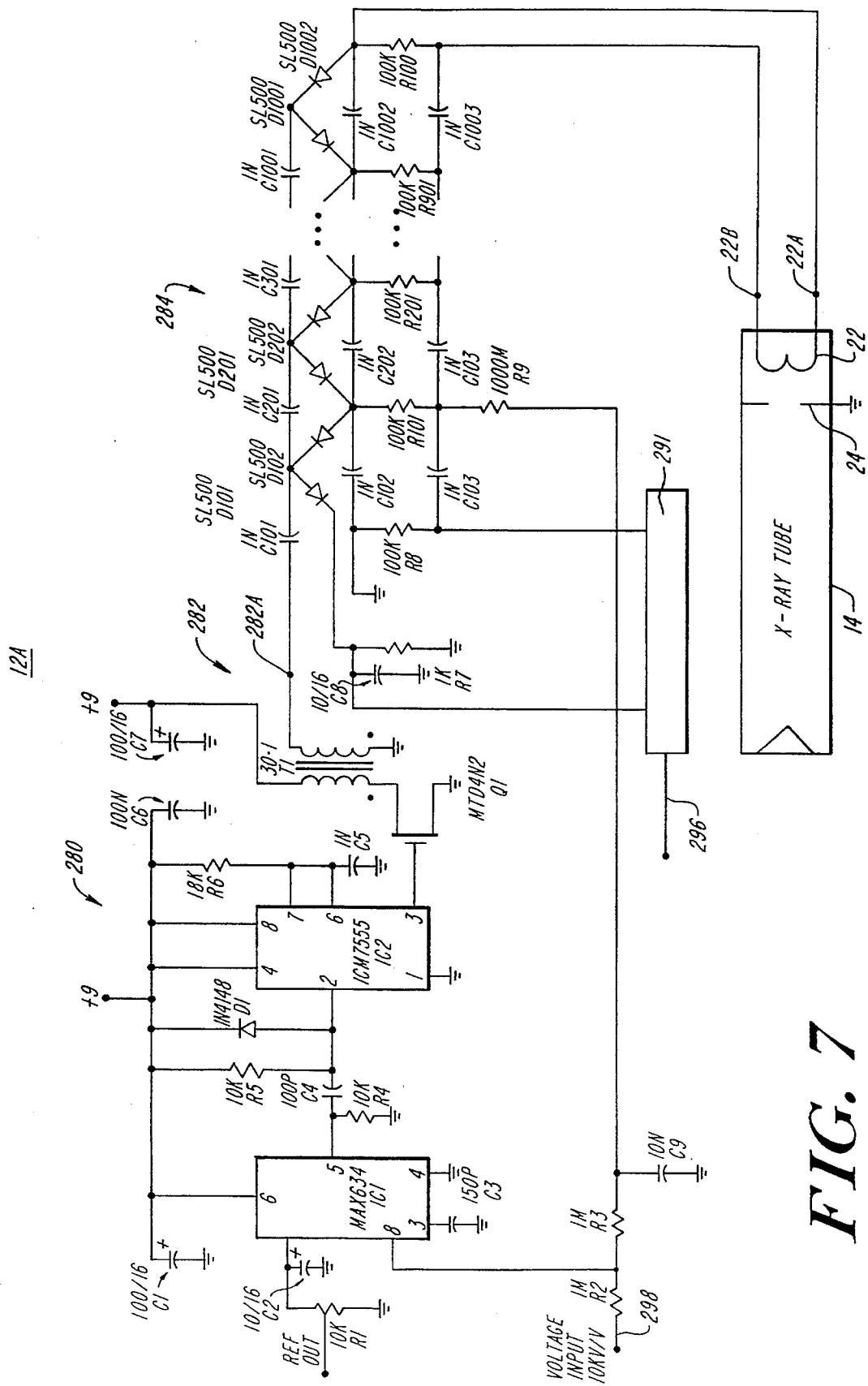
FIG. 7 is a detailed schematic diagram of power supply of FIG. 6.

The emission spatial distribution may be also shaped by altering the geometric configuration of target assembly 26. By way of example, the emission element of the target assembly 26 may be shaped such that the electrons directed from the anode will be incident at a predetermined angle or may be selectively directed to different areas of the region from which emission is to occur. As shown in the above-described embodiments, the apparatus 10 of FIG. 1 includes a power supply 12A. FIG. 6 is a block diagram of a representative supply 12A. FIG. 7 shows a more detailed schematic of the supply of FIG. 7. As shown in FIGS. 6 and 7, that embodiment includes a flyback switching converter and regulator 280, a 30:1 voltage transformer 282 coupled to a control voltage (or high voltage multiplier input) terminal 282a, and a 10 stage voltage multiplier 284 coupled to a high voltage terminal 22a, and adapted to drive the filament of a thermionic emitter 22. A filament RF power driver and voltage-to-frequency (V/F) converter 290 and an associated RF filament driver 292 are coupled through current control terminal 292a and capacitor $C_o$ by way of a filament drive circuit 286 to the filament of emitter 22.

A difference amplifier 294 establishes a current feedback loop by driving the RF power driver and V/F converter 290 in response to the detected difference between a current feedback signal on line 295 and an applied emission control signal on line 296. The latter signal may be selectively controlled to establish a desired temporal variation in the x-ray tube cathode current in filament of emitter (thermionic cathode) 22.

A high voltage amplitude feedback loop is established by the switching converter and regulator 280 in response to the detected difference between a voltage feedback signal on line 297 and an applied high voltage control signal on line 298. The latter signal may be selectively controlled to establish a desired amplitude variation of the potential at the filament of emitter (thermionic cathode) 22.

A more detailed description of the power supply shown in FIGS. 6 and 7 is provided in U.S. Pat. No. 5,153,900, and also in parent application U.S. Ser. No. 955,494.

FIG. 9 shows an exemplary system 300 adapted for x-ray treatment of brain tumors. System 300 includes a stereotactic frame 302 in combination with a low-power x-ray device 10A coupled thereto. In that configuration, x-ray device 10A is generally similar to the x-ray device 10 shown in FIG. 1, but has a cylindrical geometry. Corresponding elements of the two x-ray devices 10 and 10A are identified with the same reference designations. In general, stereotactic frames provide a fixed reference structure relative to the cranium of a patient. While the preferred embodiment described above is particularly adapted for use with this stereotactic frame, other embodiments of the invention might be similarly adapted for use with other frames or with general reference frames, for example, one establishing and operating fixture fixedly referenced to a part of the body other than the head. In the illustrated embodiment of FIG. 9, the stereotactic frame 302 is substantially similar to the Cosman-Roberts-Wells system manufactured by Radionics Inc., Burlington, Mass.

In the illustrated embodiment, the frame 302 establishes a reference XYZ coordinate system disposed about a desired origin point 0. The frame 302 includes a generally U-shaped support element 304 defining a reference plane. Four arms 306A, 306B 306C and 306D (not shown) extend out from support frame 304. Each arm has a positioning pin 308. The pins 308 extend generally towards each other from the respective distal tips of arms 306A, 306B, 306C and 306D. In use, the four pins 308 are positioned against a patient's skull to establish a fixed positional relationship between the frame 302 and the patient's cranium. Thus, the frame 302 defines the reference XYZ coordinate system with respect to the patient's cranium.

An x-ray device support member 310 is coupled to the support element 304 by way of a pair of rotational coupling assemblies 312 and a pair of linear coupling assemblies 314. The x-ray device support member 310 includes an arcuate support track 310A. An x-ray device 10 is coupled to support track 310A by a coupling assembly 316. Coupling assembly 316 provides controlled movement of the x-ray device 10 on a circular path along track 310A and between an inner limit point and an outer limit point along axes (exemplified by axis 316') extending radially inward from the circular path of arcuate track 310A toward the origin point O.

In addition, rotation about the hubs of rotational coupling assemblies 312 allows the x-ray device support member 310 to be rotatably moved about the X axis. The x-ray device support member 310 is translocatable in a direction normal to the plane defined by the X and Y axes (the X-Y plane) by movement along tracks 314A, of the linear coupling assemblies 314. In the illustrative embodiment, a T-groove in tracks 314A mates with a tenon of block 314B which is affixed to member 304, permitting linear motion in the direction perpendicular to the X-Y plane. Set screws 332 in block 314B may be adjusted to lock the x-ray device support member 310 at a set height relative to the support frame 304.

X-ray support member 310 may be moved in the direction of the Z axis by movement of the tenons extending from member 310 in tracks 304A of support element 304. A controlled position of the member 310 along the tracks 304A can be established using locking screws 334.

In addition, support element 304 can be adjustably positioned in the direction of the X axis by sliding member 304 relative to its support member 305, and may be adjustably positioned with three degrees of freedom to establish a desired location of origin point O within the skull of a patient.

Figure 8:
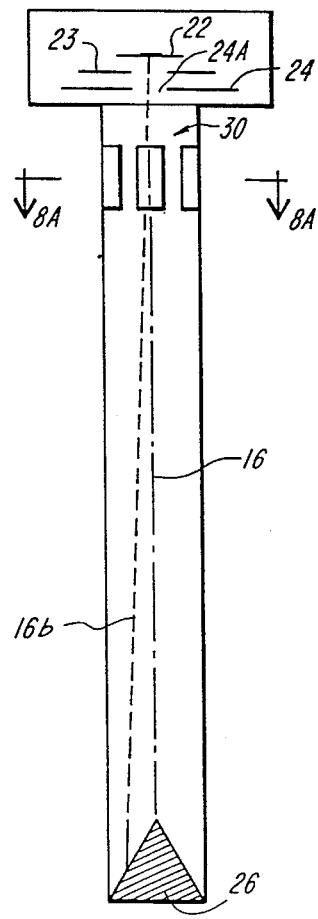
FIG. 8 is a perspective view of a beam steering assembly embodying the present invention.
Figure 8A:
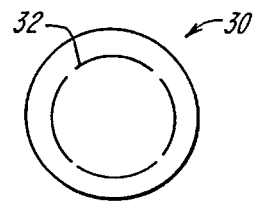
Figure 10:
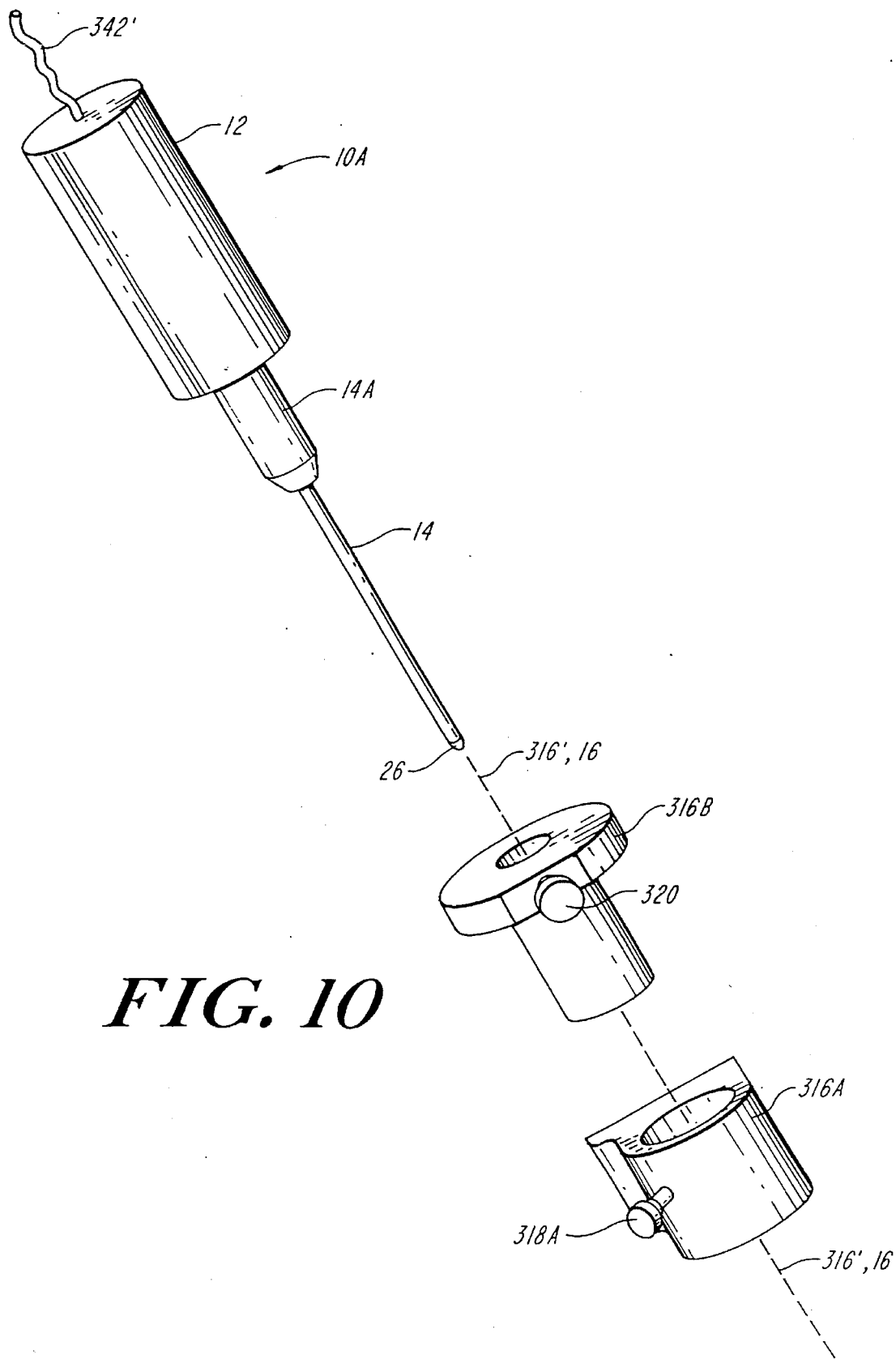
FIG. 10 is an exploded perspective view of an x-ray apparatus and the coupling assembly of the system of FIG. 9.

The coupling assembly 316 is shown together with an x-ray device 10A, in exploded form, in FIG. 10. As shown, the coupling assembly 316 includes a receiver block 316A, a bushing element 316B, together with complementary shaped portions of the x-ray device 10. As shown, the central axis of probe 14 of x-ray device 10A is coaxial with axis 316'. The electron beam axis 16 of probe 14 is nominally coaxially with axis 316', but may be adjustably varied as described above in conjunction with FIGS. 8, and 8A, and below in conjunction with FIG. 10.

The cylindrical bushing element 316B is positioned partially within and coaxially with the receiver block 316A. The bushing element 316B is slidable (in the direction of radial axis 316') and may be selectively locked in place relative to block 316A using a set screw 318A. The bushing element 316B includes a central bore (with diameter D) extending along its central axis.

As noted above, the x-ray device 10A is similar to the x-ray device 10 shown in FIG. 1, but has a generally cylindrically shaped housing 12; the probe 14 includes a cylindrical shoulder portion 14A (having a diameter slightly less than D) immediately adjacent to housing 12, with a main portion with a small diameter (3.0 mm in the preferred embodiment). With this configuration, the x-ray device 10A may be positioned with its axis 16 coaxial with axis 316' and the shoulder portion 14A slidingly positioned within the bore of bushing element 316B. The relative position of x-ray device 10A may be fixed along axis 316' using set screws 320 of element 316B.

Figure 11:
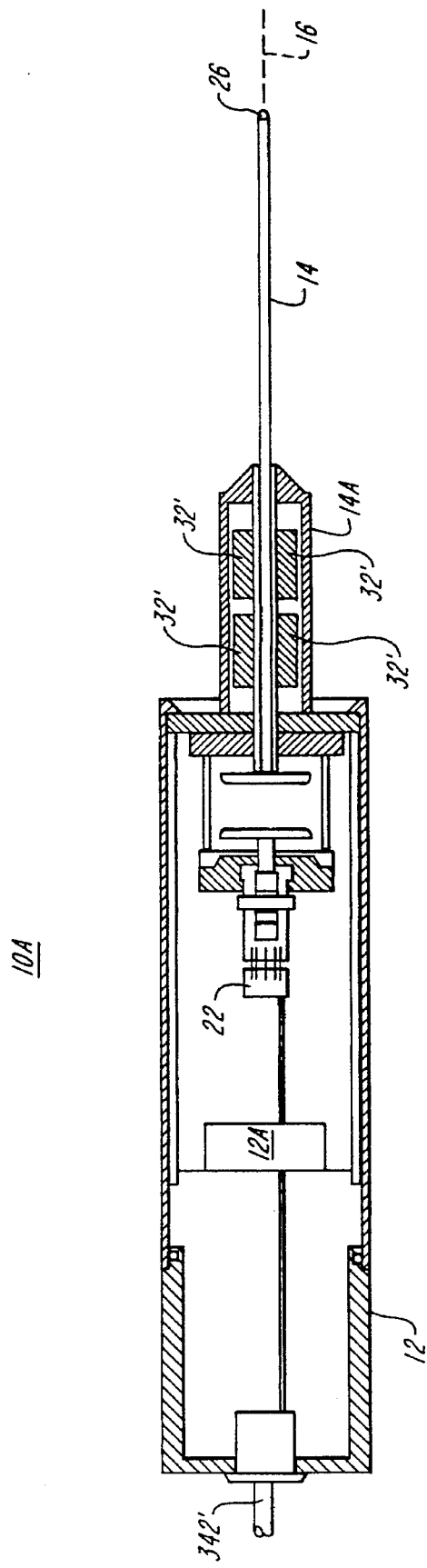
FIG. 11 is a cross-section view of the x-ray device of the system of FIG. 9.

The x-ray device 10A is shown in sectional form in FIG. 11. As shown in FIG. 11, X-ray device 10A may include a magnetic deflection subsystem for its electron beam. The deflection subsystem includes magnetic deflection coils 32' positioned about axis 16 within shoulder portion 14A. These coils are driven to adjustably control the position of the beam axis so that the beam is incident on the target of assembly 26 in a desired manner. In the preferred form, radiation generated by device 10A is monitored (for example, by an x-ray detector positioned outside the patient) and the deflector coils are driven accordingly by steering control currents on deflection X1, X2, Y1 and Y2 lines (generated in supply 12') applied to the deflection coils.

The microprocessor-based controller may not be disposed within the housing 12, but located external to the housing 12 in a control unit 342. Control unit 342 is coupled to x-ray device 10A by way of cable 342'. The elongated probe 14 of x-ray device 10 is configured so as to allow the probe 14 to pass through the track left by a biopsy needle, thereby permitting easy insertion of the probe 14 into the brain of a patient. For tumors composed of hard tissue, and where a biopsy needle smaller in width than the probe 14 is used, proper penetration into the tumor may require first widening the track left by the biopsy needle with intermediate sized needles.

With this configuration, the tip of probe 14 contains the x-ray emitting target and can be moved in and out relative to the cranial insertion site by movement along the axis 316'. The x-ray device 10A can be secured at a given position along by set screws 318A and 320. The length of probe 14 of x-ray device 10A is chosen such that the tip of probe 14, when fully inserted down to the lower limit point along the axis 316' of 316A, exactly contacts the origin point O; when the x-ray apparatus 10 is fully withdrawn to the upper limit point along axis 316', the distal tip of the probe 14 is intended to be outside the patient's skull. The coordinates of the arcuate support track 310A can be set such that the origin point O is located at the desired epicenter of irradiation. Thus, by the rotation of x-ray device 10A support member 310 and the positioning of the x-ray device 10' along the circumferential track of the arcuate support track 310A and along axis 316', a user can choose the appropriate path (preferably of least destruction) for insertion of probe 14 into a patient's skull, the tip of probe 14 always contacting the origin point O upon full insertion of the probe 14 to the lower limit point.

Figure 12:
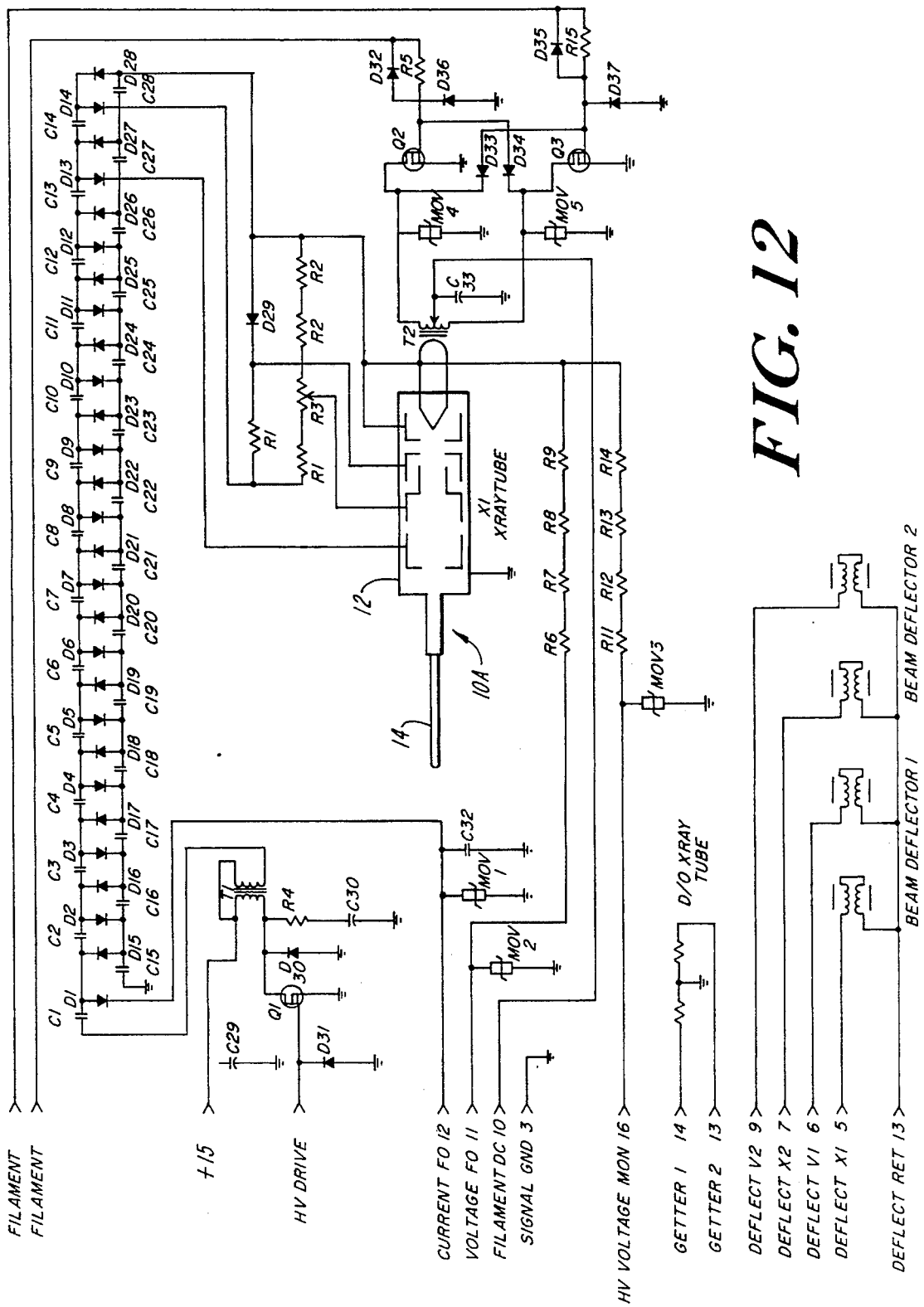
FIG. 12 is a schematic representation of the high voltage power supply of the x-ray device of the system of FIG. 9.

FIG. 12 shows a schematic diagram of a preferred high voltage power supply 12A for use with the x-ray device 10A of FIGS. 10 and 11. In that power supply, the HV drive signal is a 0 to 9 Volt pulse density modulated drive signal. This signal drives the Flyback Switching FET Q1, which in turn drives the HV Flyback transformer. The HV Flyback transformer steps up the +12 Volts to several thousand volts. The HV multiplier, D1 to D28, in turn steps up the voltage to the desired output voltage of 15 to 40 kV. The voltage FB line provides feedback information to controller 12C, so that the output voltage of the HV multiplier can be held at a constant value.

The Filament + and – lines provide complementary 9 Volt 250 kHz square wave drive signals to FET's Q2 and Q3. These FET's chop the variable Filament DC voltage into an AC voltage, and drive the Filament/HV Isolation Transformer T2. Using a high frequency signal to drive this transformer permits a single turn secondary to drive the x-ray tube filament. This in turn permits miniaturizing the transformer while maintaining the necessary high voltage isolation. The current FB line allows controller 12C to sense the beam current, and the controller then adjusts the Filament DC Voltage for the desired beam current, by providing the appropriate heating current to the thermionic emitter 22.

The Deflection X1, X2, Y1, Y2 lines provide current drive signals to the magnetic beam deflection coils.

As discussed above with respect to FIG. 1, the apparatus 10 includes beam generation and acceleration components to generate and accelerate electrons, prior to those electrons entering the probe 14. The generated electron beam then flows through probe 14, impacts the target 26b, and thereby produces x-rays. In the absence of magnetic fields, the electrons flowing through the probe 14 follow a straight-line trajectory. Consequently, the probe 14 is typically rigid without any bends.

A miniature x-ray device, such as disclosed in generally in U.S. Pat. No. 5,153,900, and U.S. Pat. application Ser. No. 955,494, has recently been developed for the purpose of treating small intracranial lesions, less than 3 cm in diameter. Unlike linear accelerators which have dual, independent, calibrated dose monitors to verify that the correct treatment dose has been given, the miniature x-ray device may not have a built-in dose monitor and may rely upon several external monitoring devices and strategies.

Figure 13:
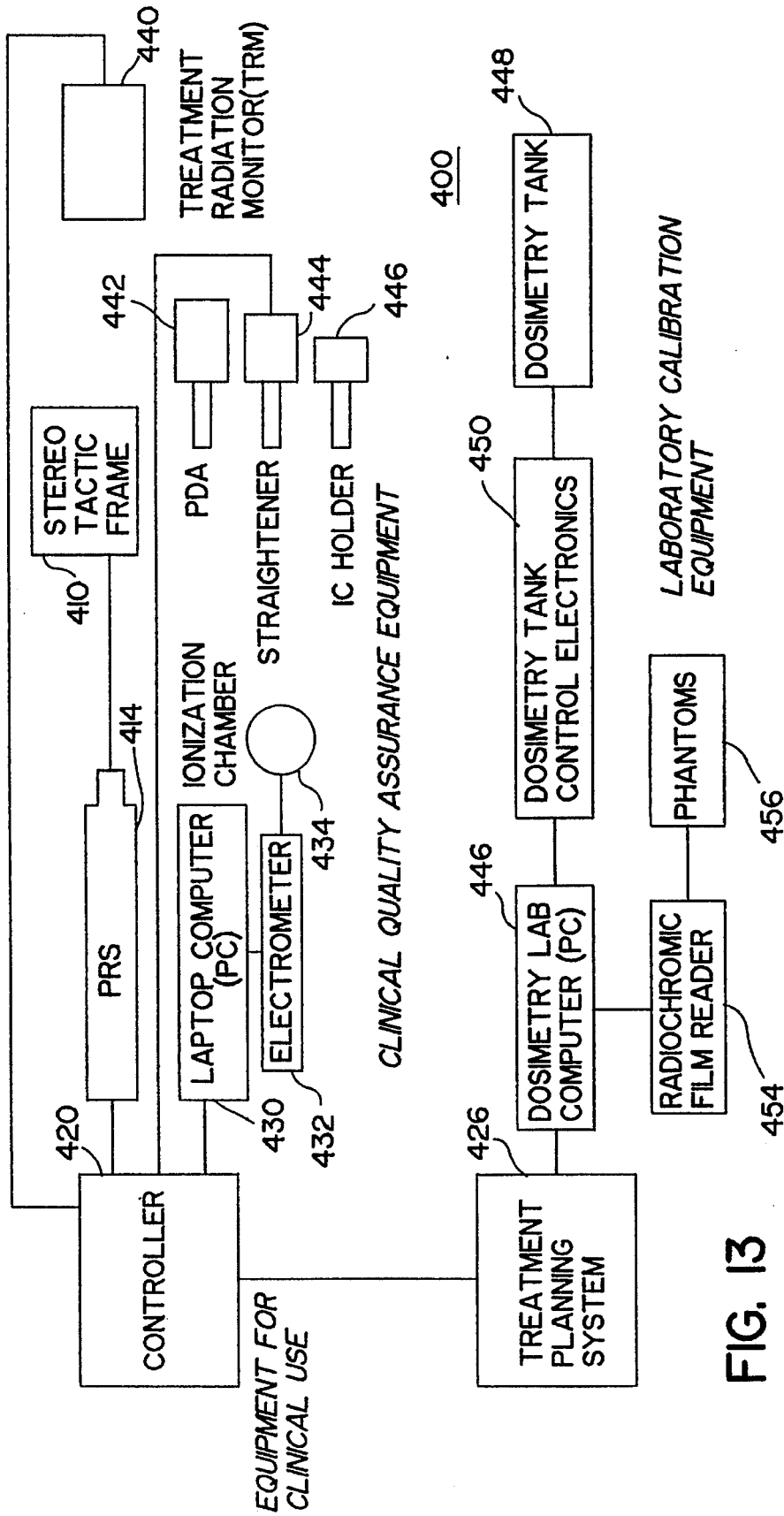
FIG. 13 shows in block diagram form, at brain tumor treatment system.
Figure 14:
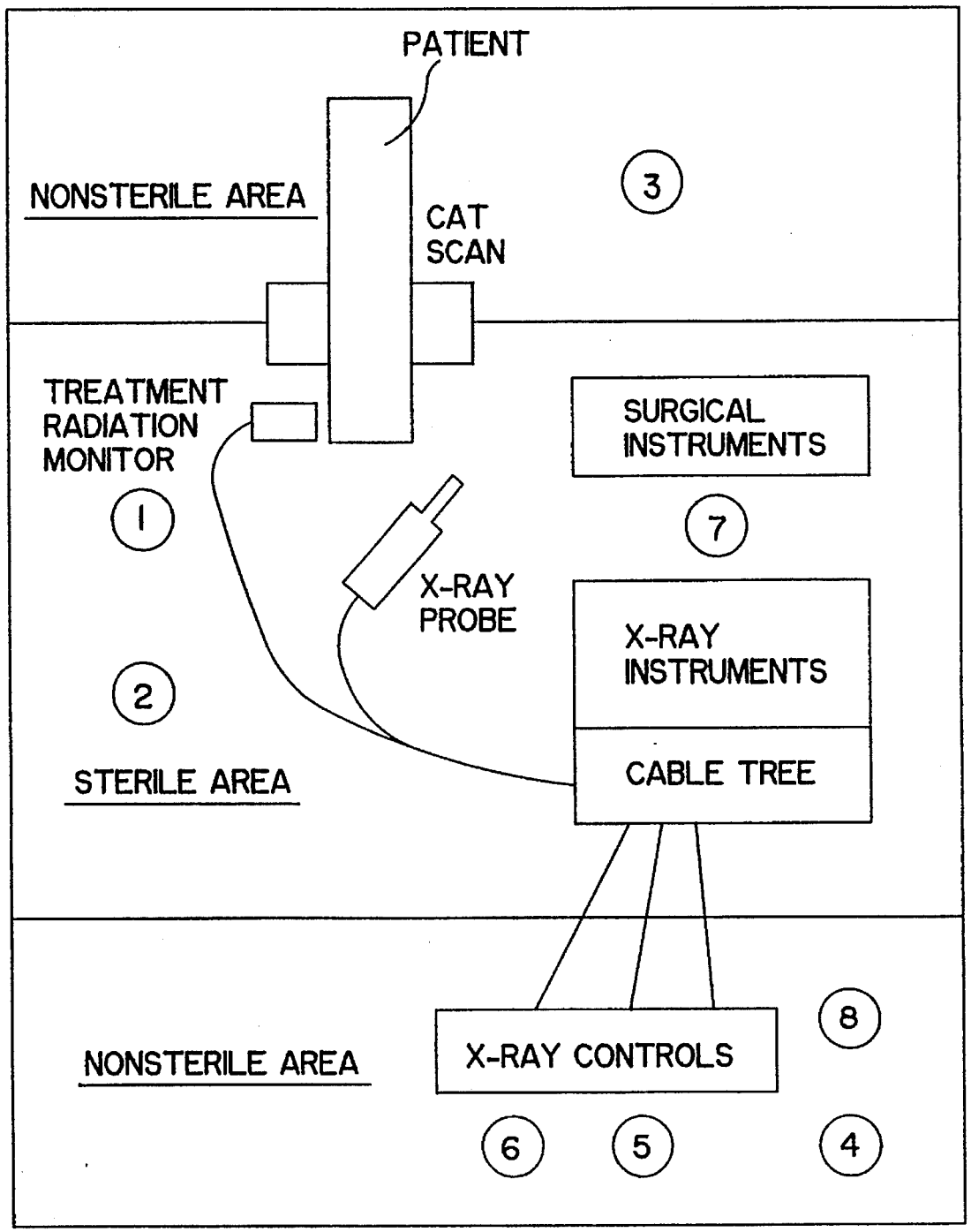
FIG. 14 shows in exemplary equipment and personnel layout for a brain tumor room.

The above described x-ray source and stereotactic frame assembly, or similar assemblies, may be used with the present invention. FIG. 13 shows, in schematic form, such a configuration (system 400) in integrated form for treating brain tumors. FIG. 14 shows a treatment room 402, showing equipment and personnel layout. System 400 includes a CRW stereotactic frame 410 affixed to a patient. The frame 410 is shown with the PRS 414 and its associated controller 420. The controller 420 is coupled to a computer based treatment planning system 426 (which evaluates CT date representative of the patient and calibration data for the PRS 414 and determines appropriate control signals for the PRS controller 420 to apply to PRS 414. As described below, the controller 420 receives calibration/monitoring data by way of a computer 430 which is coupled to an electrometer 432 which monitors an ionization chamber 434. Also, a treatment radiation monitor 440 is coupled to controller 420. A PDA 442 and straightener 444 are coupled to controller 420. The ionization chamber is supported by the ionization chamber holder (IC Holder 446).

The treatment planning system 426 is coupled to a dosimetry computer 446 which monitors a dosimetry tank 448 via associated control electronics 450. The computer 446 may monitor the output of a radiochromic film reader 454, which measures the exposure of radiochromic films, located in tissue-equivalent phantoms 456, to x-ray dose.

With this system 400, after a short warm-up of the device and check of the PRS 414 for straightness and then optimizing the output by steering adjustments to the electron beam, the dose rate of the PRS 414 in air is checked immediately prior to the procedure using a thin window, parallel plate ion chamber 434 in a fixed geometry. This dose rate is related to the dose rate in water by a transfer factor derived on previous occasions by sequential in-air and in-water measurements. This converted, in-water, dose rate is used as the basis for determining the treatment time with the PRS 414. If, the output of the PRS 414 drops, in which case, the delivered dose will be less than the prescribed dose, changes may be mad% To correct for this type of problem, should it occur, two scintillation detectors 440 are placed in the stereotactic frame close to the patient's head on either side of the x-ray device. These detectors 440 monitor the radiation during the treatment in the following way. At the beginning of the treatment the count rate from these devices is determined over a minute. Based on the prescribed treatment time, it is then possible to predict the final count at the end of the treatment. If the device should fail completely, it is possible to determine how much dose has been given, and if the dose rate should drop during the treatment, the necessary time to complete the prescribed treatment is determined.

Figure 15:
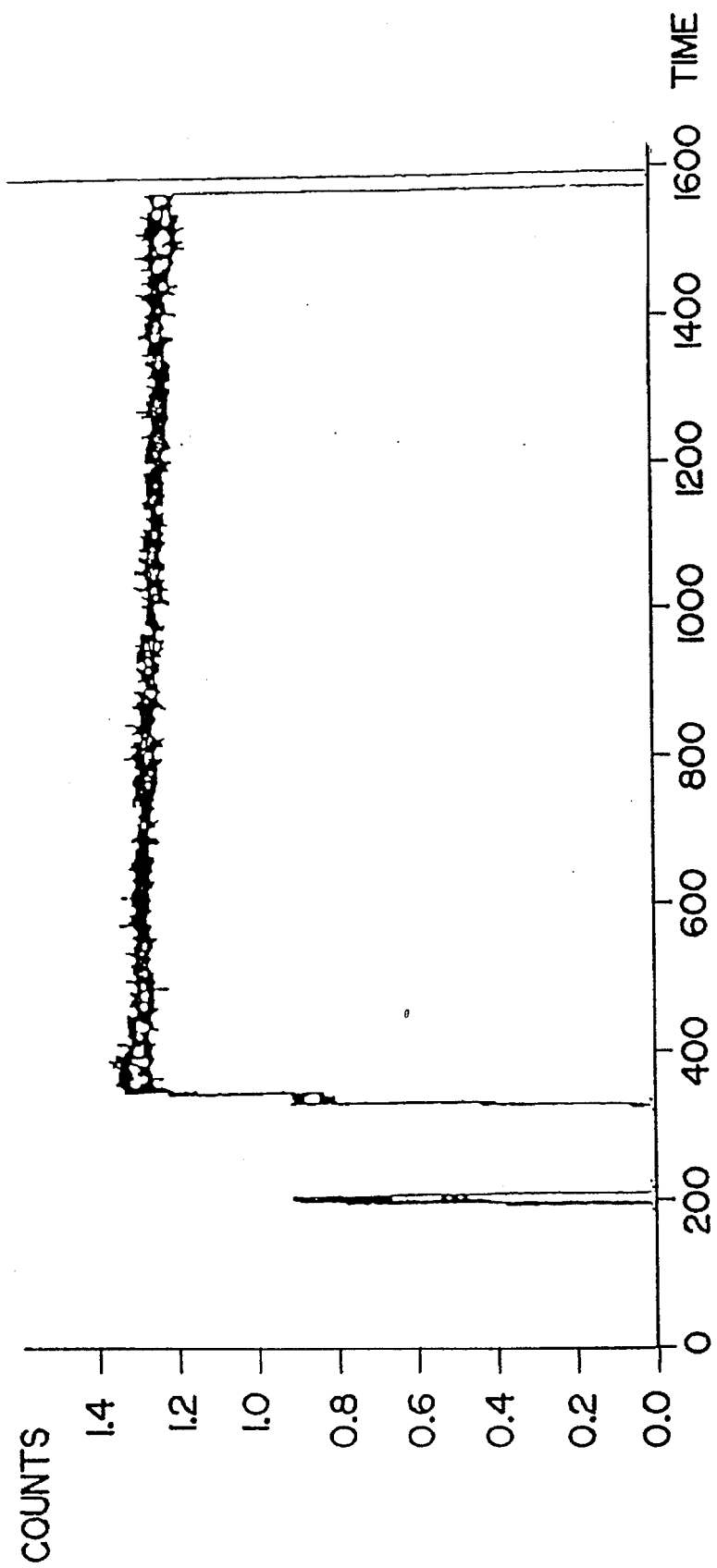
FIG. 15 shows an exemplary sweep chart of a scintillation detector in use in the system of FIG. 13.

Throughout the treatment, the count rate from both scintillation detectors is monitored graphically on a laptop PC 430. This device 430 provides the first warning of any change in the operating conditions of the PRS. FIG. 15 shows a trace of the scintillation monitor 440 count rate as displayed on the PC 430. These curves show a nearly constant output rate. The slight decay has been well characterized and is substantially constant over repeated treatments and is accounted for in the treatment time calculation. The first dose pulse shown at '200' is the period when the count rate is first sampled. This time is included in the overall treatment time.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of treating brain tumors in patient, comprising the steps of:
   A. identifying and locating a brain tumor in vivo;
   B. implanting at least a portion of an adjustable x-ray radiation source in said patient proximate to said tumor; and
   C. controlling said source to generate an x-ray radiation pattern, characterized by a spatial and temporal distribution, to selectively irradiate said tumor,
   wherein said controlling step includes the substeps of:
      i. providing at least one scintillation detector adjacent to the head of said patient and monitoring the x-rays detected by said scintillation detector, and
      ii. adjusting said sources in response to said monitoring so that the temporal and intensity pattern of said x-rays generated by said source has a predetermined form.

2. A method of treating brain tumors according to claim 1 wherein said adjustable radiation source includes an electron beam source outside the head of said patient and said implanting step includes the substep of directing an electron beam produced outside the head of said patient along said path to said location.

3. A method of treating brain tumors according to claim 1,
   wherein prior to said implanting step, performing a step of calibrating said x-ray source by measuring the x-rays produced by said source with an ion chamber.

4. A method of treating brain tumors according to claim 1,
   wherein prior to said implanting step, performing a step of calibrating said x-ray source by obtaining sequential in-air and in-water measurements for determining time of treatment.

5. A method of treating brain tumors in patient, comprising the steps of:
   A. identifying and locating a brain tumor in vivo;
   wherein said identifying and locating step includes the substeps of:
      i. affixing a stereotactic frame to the head of said patient,
      ii. performing a computer tomographic (CT) scan of the skull of said patient to determine the location, size, and shape of said tumor with respect to said stereotactic frame,
      iii. performing a biopsy by inserting a tissue extraction tool along a path measured with respect to said frame to said tumor location, extracting a tissue from said location, removing said needle and extracted tissue and analyzing said tissue, and
   B. implanting at least a portion of an adjustable x-ray radiation source in said patient proximate to said tumor, said adjustable radiation source including an electron beam source outside the head of said patient, and directing an electron beam produced by said source outside the head of said patient along said path to said location, and
   C. controlling said source to generate an x-ray radiation pattern, characterized by a spatial and temporal distribution, to selectively irradiate said tumor.

6. A method of treating brain tumors according to claim 5,
   wherein prior to said implanting step, performing a step of calibrating said x-ray source by measuring the x-rays produced by said source with an ion chamber.

7. A method of treating brain tumors according to claim 5,
   wherein prior to said implanting step, performing a step of calibrating said x-ray source by obtaining sequential in-air and in-water measurements for determining time of treatment.

* * * * *